(12) United States Patent
Martin et al.

(10) Patent No.: US 8,694,332 B2
(45) Date of Patent: Apr. 8, 2014

(54) SYSTEM AND METHOD FOR PROCESSING A PRESCRIPTION

(75) Inventors: Nathaniel G. Martin, Rochester, NY (US); Paul R. Austin, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 364 days.

(21) Appl. No.: 12/872,758

(22) Filed: Aug. 31, 2010

(65) Prior Publication Data

US 2012/0053955 A1 Mar. 1, 2012

(51) Int. Cl.
*G06Q 50/00* (2012.01)

(52) U.S. Cl.
USPC ............ 705/2; 705/3; 705/315; 600/407; 700/231; 726/4

(58) Field of Classification Search
USPC ........ 600/407; 700/231; 705/2, 315, 3; 726/4
See application file for complete search history.

(56) References Cited

U.S. PATENT DOCUMENTS

| | | | |
|---|---|---|---|
| 5,301,105 A | 4/1994 | Cummings, Jr. | |
| 6,014,631 A | 1/2000 | Teagarden et al. | |
| 6,396,951 B1 | 5/2002 | Grefenstette | |
| 6,598,799 B1 * | 7/2003 | Jang ..................... | 235/462.25 |
| 6,744,536 B2 | 6/2004 | Buchar et al. | |
| 6,850,730 B2 | 2/2005 | Adams | |
| 7,483,179 B2 | 1/2009 | Stumbo et al. | |
| 7,689,037 B2 | 3/2010 | Handley et al. | |
| 7,787,986 B2 * | 8/2010 | Pinney et al. ............... | 700/232 |
| 2003/0050802 A1 | 3/2003 | Jay et al. | |
| 2003/0063097 A1 | 4/2003 | Prabhakar et al. | |
| 2003/0161534 A1 | 8/2003 | Loce et al. | |
| 2003/0164875 A1 | 9/2003 | Myers | |
| 2004/0096102 A1 | 5/2004 | Handley | |
| 2005/0148849 A1 * | 7/2005 | Heere et al. ................. | 600/407 |
| 2005/0182656 A1 * | 8/2005 | Morey ........................ | 705/2 |
| 2007/0043469 A1 * | 2/2007 | Draper ...................... | 700/231 |
| 2007/0112460 A1 | 5/2007 | Kiselik | |
| 2007/0239504 A1 | 10/2007 | Austin et al. | |
| 2008/0055629 A1 | 3/2008 | Kovnat | |
| 2008/0091800 A1 | 4/2008 | Sorrentino et al. | |
| 2009/0006126 A1 * | 1/2009 | Champigny ............... | 705/2 |
| 2009/0299765 A1 | 12/2009 | Martin | |
| 2010/0217626 A1 | 8/2010 | Epstein et al. | |
| 2010/0280964 A1 * | 11/2010 | Register et al. ............ | 705/317 |
| 2010/0287001 A1 | 11/2010 | Pearce et al. | |
| 2010/0325698 A1 * | 12/2010 | Ginter et al. .................. | 726/4 |
| 2012/0185267 A1 | 7/2012 | Kamen et al. | |

OTHER PUBLICATIONS

Google Patents Search Results.*
Google Scholar Search Results.*
Google search, Dec. 7, 2013.*

* cited by examiner

*Primary Examiner* — Dilek B Cobanoglu
(74) *Attorney, Agent, or Firm* — Fox Rothschild LLP

(57) ABSTRACT

A system for generating a prescription may include a capture module configured to capture information from a plurality of individual cards. At least one of the cards may include medical information including at least a medication and a dosage for a patient. The system may include an information processing module configured to generate a bitmap file associated with the captured information, extract at least a portion of the medical information from the bitmap file using optical character recognition, and assemble the extracted information to generate a prescription data file. The system may include a transmission module configured to transmit the prescription data file to a pharmacy.

19 Claims, 4 Drawing Sheets

SYSTEM AND METHOD FOR PROCESSING A PRESCRIPTION

CROSS REFERENCE TO RELATED APPLICATIONS

This application is related to co-pending U.S. patent application Ser. No. 12/872,844, filed Aug. 31, 2010.

BACKGROUND

Prescription medications are a primary method of treating ailments. It is common for a physician to provide a patient with a handwritten prescription indicating a prescribed medication, dosage and dosage instructions. This information is commonly provided to a patient on a piece of paper preprinted with the physician's name and contact information. Often, the physician's handwriting is illegible or difficult to read. In addition, most patients are responsible for fulfillment of the prescriptions that are provided to them. In practice, however, a significant number of prescriptions go unfilled for a variety of reasons.

Prescriptions can also be phoned or faxed to a pharmacy, or logged using an electronic prescription system. But these approaches require substantially more time on the part of a healthcare provider than preparing a handwritten prescription, and are therefore often not used.

SUMMARY

This disclosure is not limited to the particular systems, methodologies or protocols described, as these may vary. The terminology used in this description is for the purpose of describing the particular versions or embodiments only, and is not intended to limit the scope.

As used in this document, the singular forms "a," "an," and "the" include plural reference unless the context clearly dictates otherwise. Unless defined otherwise, all technical and scientific terms used herein have the same meanings as commonly understood by one of ordinary skill in the art. All publications mentioned in this document are incorporated by reference. All sizes recited in this document are by way of example only, and the invention is not limited to structures having the specific sizes or dimensions recited below. Nothing in this document is to be construed as an admission that the embodiments described in this document are not entitled to antedate such disclosure by virtue of prior invention. As used herein, the term "comprising" means "including, but not limited to."

In an embodiment, a system for generating a prescription may include a capture module configured to capture information from a plurality of individual cards. At least one of the cards may include medical information including at least a medication and a dosage for a patient. The system may include an information processing module configured to generate a bitmap file associated with the captured information, extract at least a portion of the medical information from the bitmap file using optical character recognition, and assemble the extracted information to generate a prescription data file. The system may include a transmission module configured to transmit the prescription data file to a pharmacy.

In an embodiment, a method of generating a prescription may include capturing, by a multifunction device, information from a plurality of individual cards, where at least one of the cards includes medical information including at least a medication and a dosage for a patient, generating a bitmap file associated with the captured information, extracting at least a portion of the medical information from the bitmap file using optical character recognition, assembling the extracted information to generate a prescription data file, and transmitting, by the multifunction device, the prescription data file to a pharmacy.

DETAILED DESCRIPTION

For purposes of the discussion below, a "multifunction device" is print production equipment that is capable of performing two or more distinct document-related functions. For example, a multifunction device may have print, scan, fax and/or email capabilities. A multifunction device may be connected to a network via a communications port so that it can send information that it receives to a recipient via the network.

A "prescription" is a healthcare program under which direction is provided by a physician or other healthcare professional to a pharmacist or other healthcare professional for the preparation, dispensation and/or administration of a medication or other form of treatment.

Figure 1:
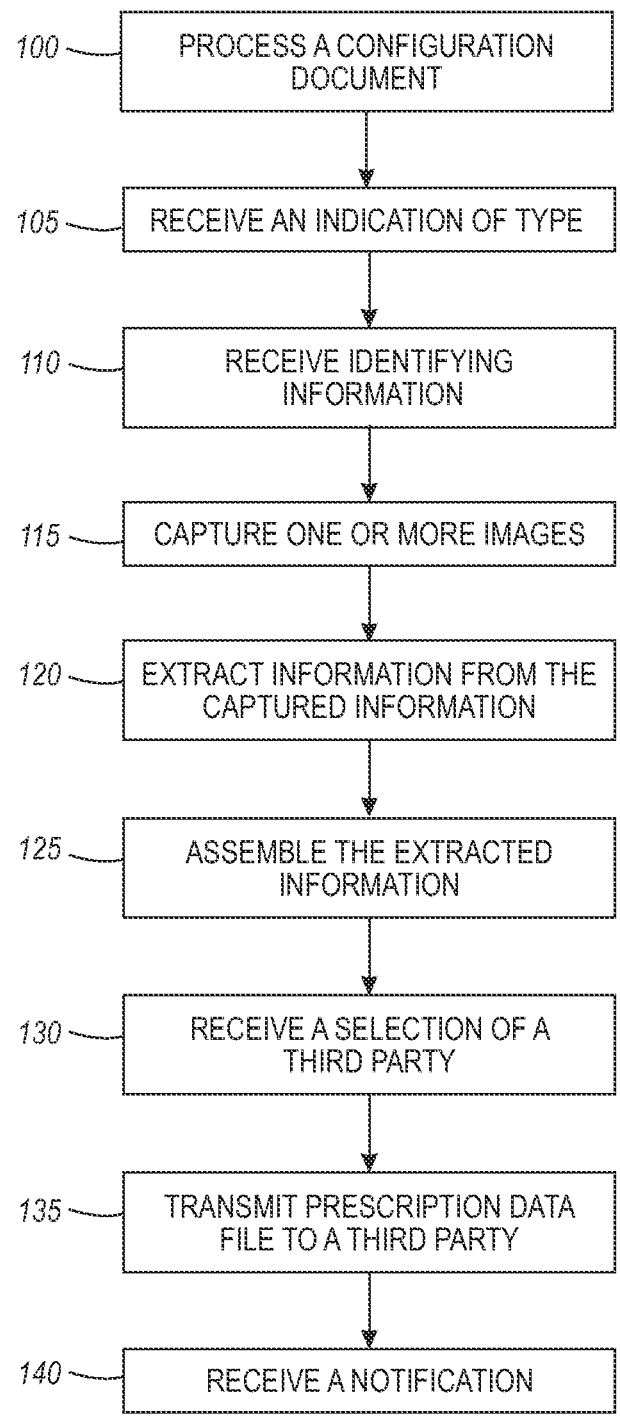
FIG. 1 illustrates an exemplary method for generating a prescription according to an embodiment.

FIG. 1 illustrates an exemplary method of generating a prescription using a multifunction device according to an embodiment. As illustrated by FIG. 1, a multifunction device may scan, read or otherwise process 100 a configuration document. A configuration document may be paper or another substrate that includes machine-readable information that, when processed by a multifunction device, will configure one or more settings of the multifunctional device to send information to a designated third party. In an embodiment, a configuration document may be an advertisement associated with a third party. A third party may be a pharmacy, a prescription fulfillment entity, a processing center, a diagnostic center, a doctor's office and/or the like.

In an embodiment, a configuration document may include human-readable information that may indicate that processing 100 the configuration document using a multifunction device. For example, the human-readable information may indicate to a reader that processing the configuration document by a multifunction device will configure one or more settings of the multifunctional device to send information to a pharmacy.

In an embodiment, the machine-readable information may include one or more transmittal instructions for communicating with a third party. The machine-readable information may include a preferred method for sending information to a third party. For example, machine-readable information may include an indication of a preferred method for sending a prescription to a pharmacy, such as but not limited to, by fax, email, FTP, regular mail and/or the like. In an embodiment, a preferred method for sending a prescription may be specified by a pharmacy, a doctor's office and/or the like. In an embodiment, machine-readable information may include contact information associated with a third party. Contact information may include a name, address, phone number, fax number, email address, IP address and/or the like associated with a third party. For example, if the preferred method for sending a prescription to a pharmacy is by fax, the machine-readable information may include the fax number for the pharmacy.

In an embodiment, a configuration document may be provided to a multifunction device user by a third party. For example, a pharmacy may send a configuration document to a doctor's office so that the office can configure its multifunction device to transmit prescriptions to the pharmacy according to the transmittal instructions contained in the configuration document. In an embodiment, a configuration document may be sent to a multifunction device user by email, fax, regular mail, hand delivery and/or the like.

Figure 2:
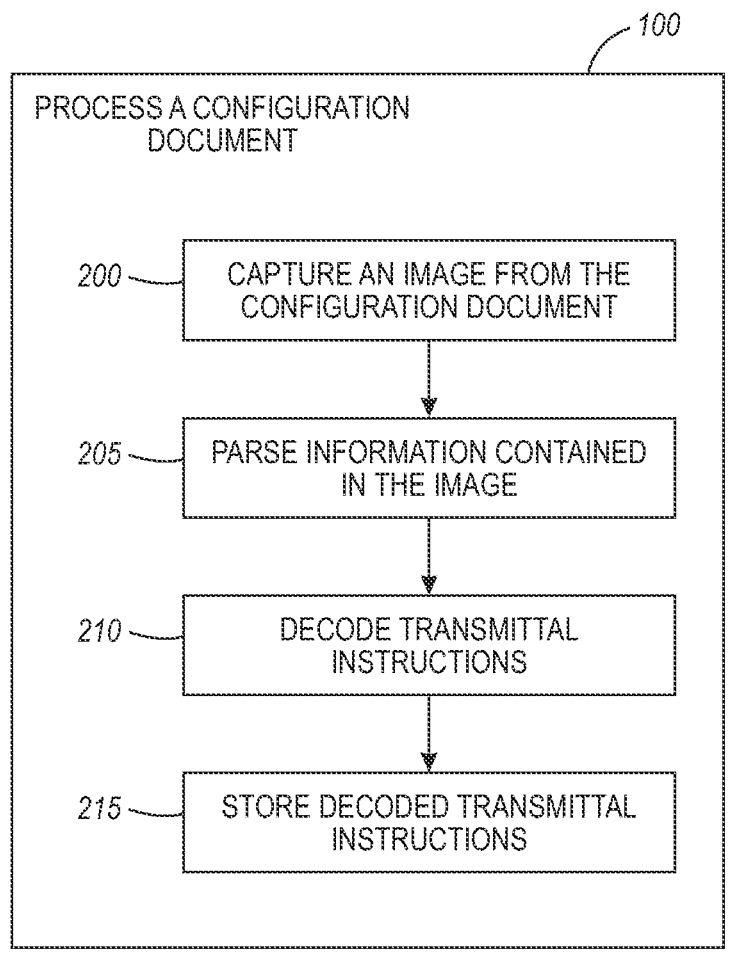
FIG. 2 illustrates an exemplary method of processing a configuration document according to an embodiment.

In an embodiment, processing 100 a configuration document may include scanning the configuration document by the multifunction device. FIG. 2 illustrates an exemplary method of processing 100 a configuration document according to an embodiment. As illustrated by FIG. 2, processing 100 may include capturing 200 an image of all or a portion of the configuration document by the multifunction device, and parsing 205 information contained in that image. For example, text in an image may be parsed 205 using any suitable pattern recognition technique now or hereafter known to those of skill in the art. As another example, an image may include a QR code that contains information that may be read and processed.

In an embodiment, an image reading module of a multifunction device may decode 210 transmittal instructions contained in the machine-readable information of a configuration document. In an embodiment, transmittal instructions may be included in a human-readable and/or machine-readable portion of the configuration document. In an embodiment, transmittal instructions may include information regarding how a multifunction device is to transmit information to a third party that generated the configuration document. For example, a pharmacy may generate and provide a configuration document to a doctor's office. The configuration document may include one or more transmittal instructions regarding how a multifunction device located at the doctor's office should transmit prescription information to the pharmacy. In an embodiment, the transmittal instructions may include one or more of the name and address of the pharmacy, the pharmacy's preferred method of receiving prescriptions, such as via fax, email, phone and/or the like, a unique identifier associated with the pharmacy, and/or the like.

In an embodiment, at least a portion of the decoded transmittal instructions may be stored 215 by a multifunction device. For example, a multifunction device may maintain a database that includes one or more transmittal instructions associated with each of the configuration documents it has processed 100. Table 1 illustrates exemplary data elements in a database according to an embodiment.

TABLE 1

| Pharmacy | Preferred Method of Contact | Contact Information |
| --- | --- | --- |
| Rite Aid | Fax | 555-2314 |
| Medco | FTP | 12.132.22.312 |
| Wegmans | Email | rx@wegmans.com |
| Walgreens | Electronic, HL7 | RochRHIO::Walgreens14 |
| Mail Pharm | Mail | Mail Pharm |
| | | 123 Main Street |
| | | Anytown, USA 00000 |

In an embodiment, the stored transmittal instructions may be used to automatically send information to a third party. For example, a list of one or more pharmacies for which associated configuration documents have been received may be displayed to a user, such as a doctor, nurse or other healthcare provider. In an embodiment, the list may be displayed to a user on a computing device in communication with a multifunction device that has processed configuration documents associated with one or more pharmacies. A user may select a pharmacy to which a prescription is to be sent by using a touch screen or other input device, such as a mouse, a keyboard and/or the like. A prescription or other information may be automatically sent to the selected pharmacy in accordance with the preferred method of contact associated with the selected pharmacy and stored on the multifunction device. For example, referring back to Table 1, if a nurse selects Wegmans as the pharmacy, a prescription may automatically be emailed to rx@wegmans.com.

In an embodiment, one or more third parties associated with a configuration document that has been processed by a multifunction device may be removed from memory of the multifunction device. For example, a doctor's office may remove a pharmacy from its multifunction device if the pharmacy closes. In an embodiment, information associated with a third party may be removed from a multifunction device by identifying the third party using a computing device, and providing an indication that this third party should be removed from the system. For example, a healthcare provider may select a pharmacy from a list of available pharmacies by highlighting the pharmacy or otherwise selecting a pharmacy using a touch screen, keyboard, mouse and/or the like. In an embodiment, a healthcare provider may enter the name of the pharmacy to be removed. In another embodiment, a healthcare provider may scan the configuration document associated with the pharmacy to be removed using a multifunction device to identify the pharmacy. The healthcare provider may press a button, make a selection from a drop-down list, or otherwise indicate that the selected pharmacy is to be removed from the system, at which time information associated with the selected pharmacy may be erased from the memory of the multifunction device.

In an embodiment, a multifunction device may be used to generate and/or transmit a information. As illustrated by FIG. 1, an indication of a type associated with information to be transmitted may be received 105 by a multifunction device. For example, a healthcare provider may provide an indication that the information to be transmitted is a prescription. In an embodiment, a user may provide this indication directly to a multifunction device, such as by pressing a button on the multifunction device, making a selection from one or more menus on a display of the multifunction device and/or the like. In an embodiment, a user may provide an indication of information type to a computing device in communication with a multifunction device.

In an embodiment, a multifunction device may receive 110 identifying information from a user of the multifunction device. For example, a doctor, nurse or other healthcare professional may be required to enter a personal identification number, a password and/or the like to access the multifunction device. The received identifying information may be compared to identifying information stored in the multifunction device's memory, or in a storage medium in communication with the multifunction device. If the provided identifying information matches the stored information, the multifunction device may allow the user access to the multifunction device. If the provided identifying information does not match the stored information, the multifunction device may not allow the user access to the multifunction device.

As illustrated by FIG. 1, one or more images may be captured 115 from one or more individual cards by a multifunction device. In an embodiment, a card may be a portion of paper or other substrate that contains patient information, physician information, pharmacy information, prescription information and/or the like.

In an embodiment, patient identification information may include information such as a patient's name, address, telephone number, email address, birth date, insurance provider, insurance group number, co-pay information, insurance provider contact information and/or the like. Physician information may include information such as a physician's name, address, telephone number and/or the like. Pharmacy information may include a name of a pharmacy where a prescription is to be filled, the pharmacy's address, phone number, email address and/or the like. Prescription information may include a prescribed medication, a prescribed dosage, dosage instructions and/or other information regarding a prescribed medication. Exemplary cards may include a drivers license, an insurance card, a prescription card, a Medicare card, a Medicaid card, a medical identification card, a business card, a handwritten prescription and/or the like. Additional and/or alternate cards may be used within the scope of this disclosure.

In an embodiment, information may be captured 115 from a card using a multifunction device. For example, a multifunction device may capture 115 information from a card by scanning at least a portion of the card. A card may be placed into a sheetfed scanner of the multifunction device. In an embodiment, a card may be scanned from a platen of the multifunction device. In an embodiment, a digital bitmap representing the scanned platen area may be generated. In an embodiment, a multifunction device may capture 115 information from a card by photographing at least a portion of the card. Additional and/or alternate image recording techniques may be used within the scope of this disclosure.

In an embodiment, a multifunction device may capture 115 information from multiple cards. The information may be captured 115 from the cards simultaneously. For example, multiple cards may be scanned from a platen of a multifunction device simultaneously. In an embodiment, information may be captured 115 from multiple cards consecutively. For example, a patient's driver's license may be scanned using a sheet feeder of a multifunction device. Subsequently, the patient's insurance card may be scanned using the sheet feeder of the multifunction device.

In an embodiment, a multifunction device may extract 120 a subset of information from the captured information. For example, information may be parsed from captured information. Exemplary methods for parsing information are described in U.S. patent application Ser. No. 10/970,930, filed Oct. 22, 2004 entitled "System and Method for Identifying and Labeling Fields of Text Associated with Scanned Business Documents," U.S. Patent Application Publication No. 2004/0096102 entitled "Methodology for Scanned Color Document Segmentations"; U.S. Patent Application Publication No. 2003/0161534 entitled "Feature Recognition Using Loose Gray Scale Template Matching"; and U.S. Patent Application Publication No. 2003/0063097 entitled "Detection and Segmentation of Sweeps in Color Graphic Images," the disclosures of which are herein incorporated by reference.

In an embodiment, information may be extracted 120 using optical character recognition. For example, a digital bitmap corresponding to one or more scanned cards may be processed using any optical character recognition now or hereafter known to those of skill in the art. Optical character recognition may be any conventional optical character recognition process such as that described in U.S. Pat. No. 6,396,951, the entirety of which is incorporated by reference. Optical character recognition may convert each bit map into text data. One or more fields of text data may be extracted from the cards. In an embodiment, each field may correspond to a label, for example, name, address, social security number and/the like.

In an embodiment, a multifunction device may use one or more keys associated with at least a portion of captured information to obtain prescription information from a database. For example, a multifunction device may use a group number from captured information, or from a bitmap file associated with captured information, of a patient's insurance card to obtain insurer information to include in a prescription. In an embodiment, a multifunction device may extract 120 information from a machine readable portion of a recorded image. For example, captured information from of a card may include a barcode, a glyph or other machine readable code. A multifunction device may translate machine readable information into human readable information that is to be included in a prescription. In an embodiment, a multifunction device may extract 120 information from a captured image using optical character recognition.

In an embodiment, information may be extracted 120 from the memory of the multifunction device. In an embodiment, a multifunction device may store information that is common to each prescription, such as physician information, in its memory. For example, a physician's name, address, digital signature and/or the like may be preprogrammed into the multifunction device so that this information can be extracted 120 with each prescription that is generated.

In an embodiment, the extracted information may be assembled 125 by a multifunction device to create a prescription data file. A prescription data file is a digital file containing data representing characteristics of a prescription. For example, a prescription data file may include information representing a prescribed medication, a dosage associated with the medication, a patient to whom the medication is prescribed, one or more instructions of administering the medication and/or the like. In an embodiment, the extracted information may be assembled 125 into a prescription data file using a template. For example, extracted information may be inserted into one or more designated locations within a template. Alternatively, extracted information may be assembled into a prescription data file without the use of a template.

In an embodiment, a selection of a third party may be received 130. The selected third party may be one to which the prescription is to be sent. For example, a selection of a pharmacy that is to fill a particular prescription may be received 130. In an embodiment, a selection may be received 130 from a user of a multifunction device. In an embodiment, a user may select a third party by entering, via a multifunction device and/or computing device in communication with a multifunction device, a name or other identifying information corresponding to the third party.

In an embodiment, a list of some or all of third parties to which a multifunction device has been configured to transmit information may be displayed to a user. In an embodiment, information associated with one or more third parties may be stored in a database. For example, a name, address and phone number associated with a third party may be stored in a database. In an embodiment, the database may be a component of the multifunction device. Alternatively, the database may be in communication with the multifunction device, but located externally from the multifunction device. In an embodiment, a list of third parties may be displayed on a display device. A display device may be a component of a multifunction device. Alternatively, a display device may be in communication with a multifunction device but located externally from the multifunction device.

In an embodiment, a user may select a third party from a displayed list, and the user's selection may be received 130 by a multifunction device. A user may make a selection using one or more buttons, keys, touch pads and/or other input devices of a multifunction device. Alternatively, a user may make a selection using a mouse, keyboard or other similar input device of a computing device.

In an embodiment, a selection of a third party may be received 130 by processing a batch sheet. A batch sheet may be a portion of paper or other substrate that may include human-readable information and/or machine-readable information. Human-readable information may indicate the third party to which a prescription should be sent and/or one or more transmittal instructions for sending a prescription to the third party. In an embodiment, machine-readable information may include an indication of a name of a third party to which the prescription should be sent and/or one or more transmittal instructions.

In an embodiment, a multifunction device may print one or more batch sheets associated with one or more third parties stored in its database. For example, a multifunction device may be configured to send information to a third party through the use of a configuration document. Once the multifunction device is configured, it may print a batch sheet corresponding to the third party. The batch sheet may be used to transmit information to the third party.

In an embodiment, a prescription data file may be transmitted 135 to a third party. For example, a prescription data file may be transmitted 135 to a pharmacy, a processing center, a diagnostic center, a doctor's office and/or the like. In an embodiment, the prescription data file may be transmitted 135 to a third party via email, fax, scan and/or the like.

In an embodiment, a prescription data file may be transmitted 135 to a third party according to the transmittal instructions associated with the third party that are stored in a multifunction device. For example, referring to Table 1, if a user selects a particular Rite Aid location as the third party, then a prescription data file may be faxed to the number 555-2314, which corresponds to the fax number for that location. In an embodiment, a batch file may be used to transmit 135 a prescription data file to a third party. For example, a multifunction device may process a batch sheet provided by a user, and may send a prescription data file to third party according to one or more transmittal instructions included on the batch sheet.

In an embodiment, a third party may analyze a received prescription. For example, a received prescription may be cross-checked against other prescriptions received by the third party for the same patient to determine whether any potential drug interactions exist. In an embodiment, a received prescription may be cross-checked against other prescriptions received by the third party for the same patient and/or at least a portion of the patient's medical records to determine whether the patient is allergic to medication described in the received prescription. In an embodiment, a received prescription may be checked to determine whether the dosage and/or dosage instructions are correct. For example, a prescription may be checked to confirm that the prescribed medication is available in the prescribed dosage.

If a problem is detected with the prescription, a notification may be received 140 from the third party. For example, if the third party detects a possible drug allergy, it may notify the prescribing physician by sending a notification via email, fax, scan, telephone and/or the like. In an embodiment, a notification may be received 140 by the multifunction device.

In an embodiment, a prescription may be analyzed by a third party very shortly after receiving it. In turn, if a problem is detected with the prescription, a notification may be received from the third party very soon after the prescription was sent. As such, a problem with a prescription can be communicated to the prescribing physician and/or the patient shortly after the prescription was sent, and possibly while the patient is still at the physician's office. Any problem with the prescription may be quickly corrected by a physician. In an embodiment, an updated prescription may be sent back to the third party.

In an embodiment, the third party may fill the prescription. In an embodiment, the third party may submit the prescription for fulfillment. For example, if no problems are detected with the prescription, the third party may fill the prescription and/or submit the prescription to be filled. In an embodiment, the third party may notify the prescribing physician if a prescription is not picked up by the patient within a certain period of time. For example, if a patient has not picked up a prescription within three days of it being prescribed, the third party may notify the prescribing physician. In an embodiment, the prescribing physician may receive a notification via email, fax, scan, telephone and/or the like. In an embodiment, a notification may be received 140 by the multifunction device.

Figure 3:
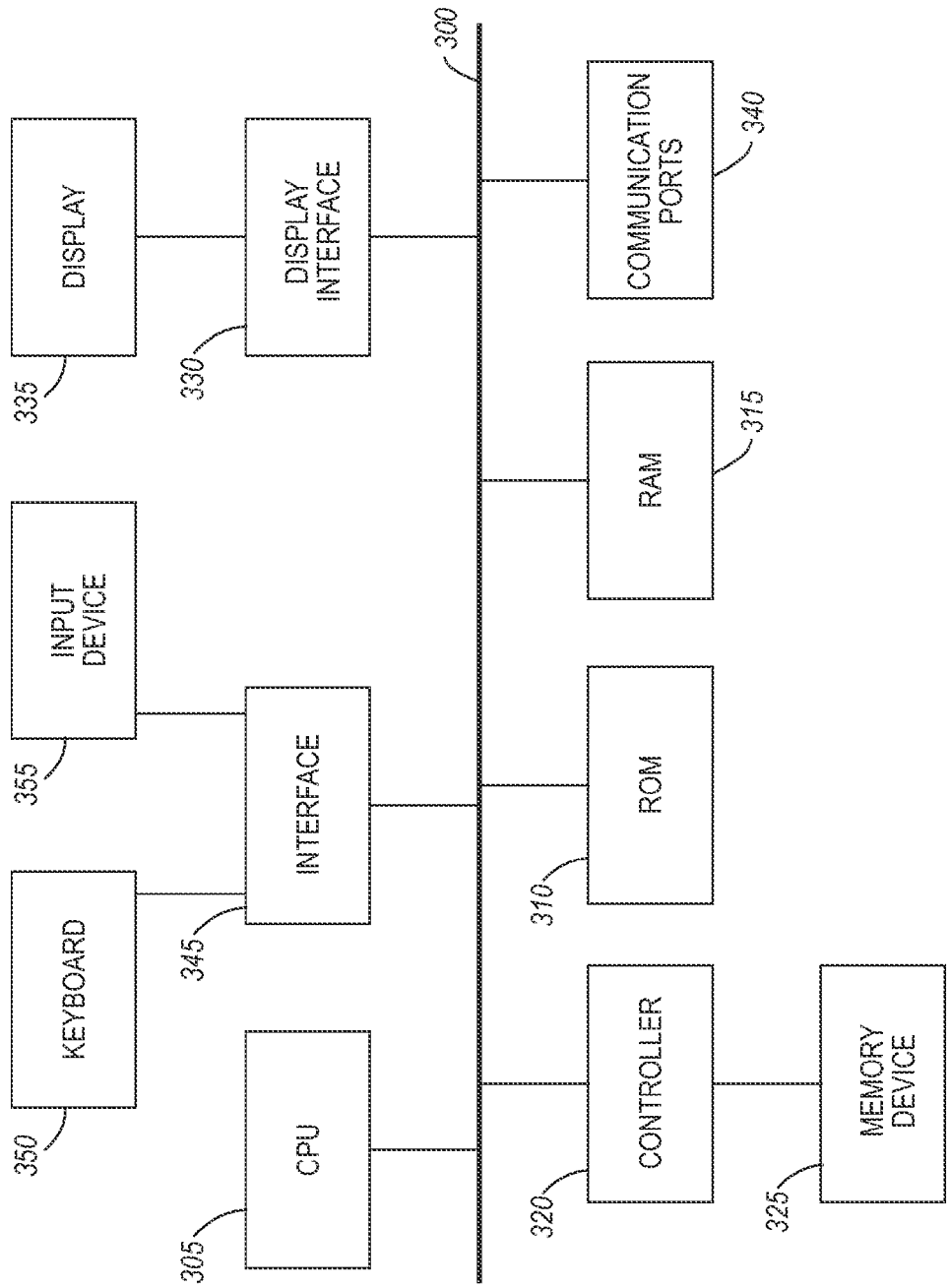
FIG. 3 illustrates a block diagram of exemplary internal hardware that may be used to contain or implement program instructions according to an embodiment.

FIG. 3 depicts a block diagram of exemplary internal hardware that may be used to contain or implement program instructions according to an embodiment. A bus 300 serves as the main information highway interconnecting the other illustrated components of the hardware. CPU 305 is the central processing unit of the system, performing calculations and logic operations required to execute a program. Read only memory (ROM) 310 and random access memory (RAM) 315 constitute exemplary memory devices.

A controller 320 interfaces with one or more optional memory devices 325 to the system bus 300. These memory devices 325 may include, for example, an external or internal DVD drive, a CD ROM drive, a hard drive, flash memory, a USB drive or the like. As indicated previously, these various drives and controllers are optional devices.

Program instructions may be stored in the ROM 310 and/or the RAM 315. Optionally, program instructions may be stored on a tangible computer readable storage medium such as a compact disk, a digital disk, flash memory, a memory card, a USB drive, an optical disc storage medium, such as Blu-ray™ disc, and/or other recording medium.

An optional display interface 330 may permit information from the bus 300 to be displayed on the display 335 in audio, visual, graphic or alphanumeric format. Communication with external devices may occur using various communication ports 340. An exemplary communication port 340 may be attached to a communications network, such as the Internet or an intranet.

The hardware may also include an interface 345 which allows for receipt of data from input devices such as a keyboard 350 or other input device 355 such as a mouse, a joystick, a touch screen, a remote control, a pointing device, a video input device and/or an audio input device.

An embedded system, such as a sub-system within a xerographic apparatus, may optionally be used to perform one, some or all of the operations described herein. Likewise, a multiprocessor system may optionally be used to perform one, some or all of the operations described herein.

Figure 4:
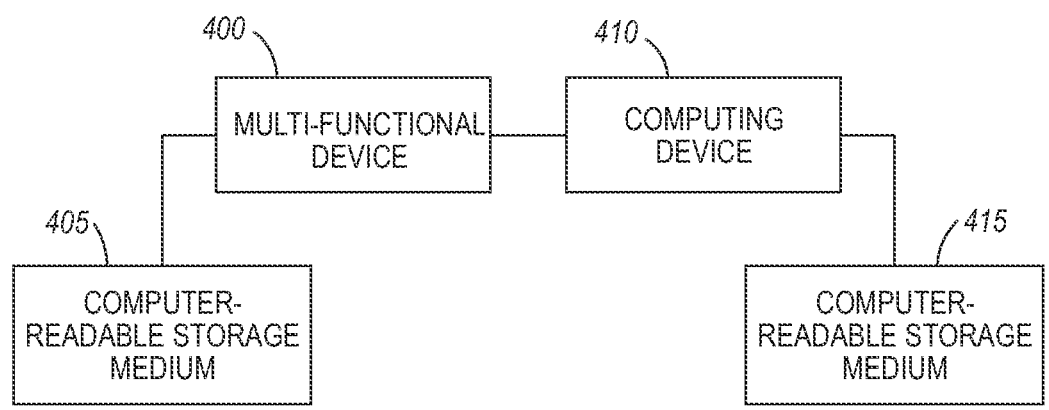
FIG. 4 illustrates an exemplary system for creating a prescription according to an embodiment.

FIG. 4 illustrates an exemplary system for creating a prescription according to an embodiment. As illustrated by FIG. 4, the system may include a multifunction device 400 and a computer-readable storage medium 405. In an embodiment, the multifunction device 400 may be in communication with the computer-readable storage medium 405. The multifunction device 400 and computer-readable storage medium 405 may be located in a physician's office, a hospital, a clinic or other location where patients may be diagnosed and/or treated.

In an embodiment, the system may include a computing device 410 in communication with a computer-readable storage medium 415. The computing device 410 may be in communication with the multi-functional device 400. As described above, the computing device 410 may receive a prescription from the multifunction device 400. In an embodiment, the computing device 410 may analyze the prescription and/or generate a notification if a problem with the prescription is detected. In an embodiment, the computing device 410 may be located at a third party location. As discussed above, a third party location may be a pharmacy, a processing center, a diagnostic center, a doctor's office and/or the like. In an embodiment, the computer-readable storage medium 415 may be located at the third party location. Alternatively, the computer-readable storage medium 415 may be located remote from the third party location.

Figure 5:
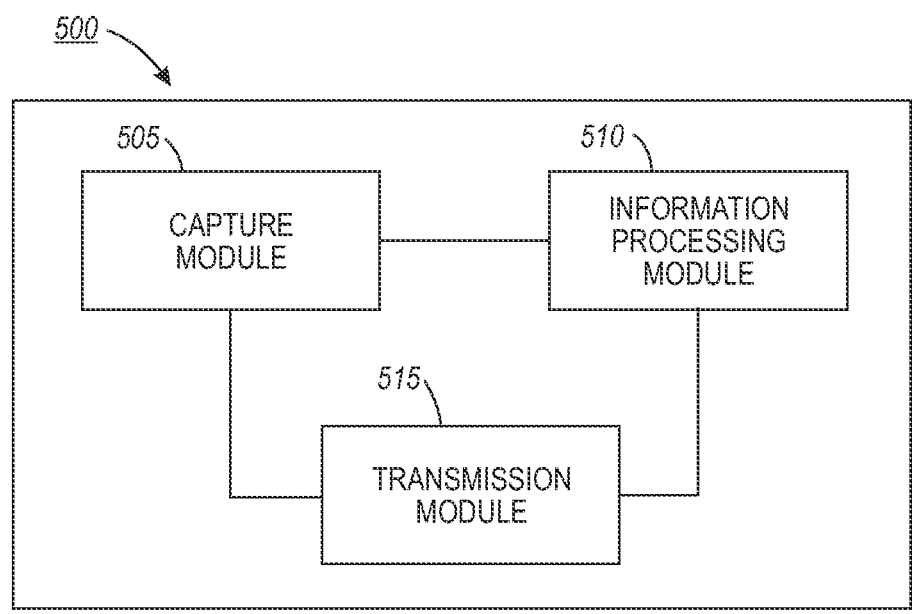
FIG. 5 illustrates an exemplary system for creating a prescription according to an embodiment.

FIG. 5 illustrates an exemplary multifunction device according to an embodiment. As illustrated by FIG. 5, a multifunction device 500 may include a capture module 505, an information processing module 510 and a transmission module 515. The capture module 505 may capture information from cards. In an embodiment, the information processing module 510 may generate a bitmap associated with captured information. The information processing module 510 may extract information from a bitmap file and may assemble the extracted information to generate a prescription data file. In an embodiment, the transmission module 515 may transmit information to and/or receive information from a third party. In an embodiment, the capture module 505, the information processing module 510 and/or the transmission module 515 may be a self-contained hardware and/or software component of a multifunction device 500. For example, a software module may be a self-contained portion of code that carries out a specific function or task. A hardware module may be one or more self-contained circuits that perform a specific function or task.

Exemplary multifunction devices include the Xerox WorkCenters. The elements of image reading modules in various multifunction devices are known and are disclosed in, for example, U.S. Pat. Nos. 6,850,730 and 6,744,536, the disclosures of which are each incorporated herein by reference in their entirety. An image sending module includes programming instructions that send data representing a received document to an external recipient via a communications port.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A multifunction device for generating a prescription, the multifunction device comprising:
   a processor; and
   a processor-readable non-transitory storage medium comprising:
      a capture module configured to capture information from a plurality of individual cards, wherein at least one of the cards comprises prescription information comprising at least a medication and a dosage for a patient,
      an information processing module in communication with the capture module, wherein the information processing module is configured to:
         identify a key from the captured information,
         use the key to retrieve additional prescription information from a database,
         generate a bitmap file associated with the captured information,
         extract at least a portion of the prescription information from the bitmap file using optical character recognition,
         extract physician information from a computer-readable memory,
         assemble the prescription information, the additional prescription information and the physician information to generate a prescription data file, and
         process a batch sheet associated with a pharmacy, wherein the batch sheet comprises machine-readable information comprising identification information for the pharmacy and one or more transmittal instructions associated with the pharmacy; and
      a transmission module in communication with the information processing module, wherein the transmission module is configured to transmit the prescription data file to the pharmacy in accordance with the transmittal instructions.

2. The multifunction device of claim 1, wherein the capture module is further configured to capture information from one or more of the following:
   a drivers license;
   an insurance card;
   a prescription card;
   a Medicare card;
   a Medicaid card;
   a medical identification card; and
   a business card.

3. The multifunction device of claim 1, wherein the capture module is further configured to simultaneously scan one or more images from the plurality of individual cards.

4. The multifunction device of claim 1, wherein the capture module is further configured to photograph one or more images from the plurality of individual cards.

5. The multifunction device of claim 1, wherein the information processing module is further configured to translate machine-readable information of the captured information to generate the prescription data file.

6. The multifunction device of claim 1, wherein the information processing module is further configured to extract prescription information from a computer-readable storage medium in communication with the system.

7. The multifunction device of claim 1, wherein the information processing module is further configured to insert the extracted prescription information into a template to create the prescription data file.

8. The multifunction device of claim 1, wherein the transmission module is further configured to transmit the prescription data file by one or more of the following:
   faxing the prescription data file to the pharmacy;
   emailing the prescription data file to the pharmacy; and
   scanning the prescription data file.

9. The multifunction device of claim 1, wherein the transmission module is further configured to receive a notification of a problem associated with the prescription data file.

10. The multifunction device of claim 9, wherein the transmission module is further configured to receive a notification that a possible drug interaction exists.

11. The multifunction device of claim 9, wherein the transmission module is further configured to receive a notification that a patient to whom the medication is prescribed is allergic to the medication.

12. The multifunction device of claim 9, wherein the transmission module is further configured to receive a notification that the medication is not available in the dosage.

13. The multifunction device of claim 9, wherein the transmission module is further configured to receive a notification that a prescription associated with the prescription data file was not picked up by the patient within a period of time.

14. A method of generating a prescription, the method comprising:
    capturing, by a multifunction device, information from a plurality of individual cards, wherein one or more of the cards comprises:
        prescription information comprising at least a medication and a dosage for a patient, and
        patient information;
    identifying a key from the captured information,
    using the key to retrieve additional prescription information from a database,
    generating a bitmap file associated with the captured information;
    extracting at least a portion of the prescription information from the bitmap file using optical character recognition;
    extracting physician information from a computer-readable memory,
    assembling the prescription information, the additional prescription information, the patient identification information and the physician information to generate a prescription data file;
    processing a batch sheet associated with a pharmacy, wherein the batch sheet comprises machine-readable information comprising identification information for the pharmacy and one or more transmittal instructions associated with the pharmacy; and
    transmitting, by the multifunction device, the prescription data file to the pharmacy in accordance with the transmittal instructions.

15. The method of claim 14, wherein extracting at least a portion of the prescription information comprises translating machine-readable information in the bitmap file to generate the prescription data file.

16. The method of claim 14, wherein extracting at least a portion of the prescription information comprises retrieving the prescription information from a computer-readable storage medium in communication with the multifunction device.

17. The method of claim 14, further comprising receiving, by the multifunction device, a notification of a problem associated with the prescription data file, wherein the notification comprises one or more of the following:
    notification that a possible drug interaction exists;
    notification that a patient to whom the medication is prescribed is allergic to the medication;
    notification that the medication is not available in the dosage; and
    notification that a prescription associated with the prescription data file was not picked up by the patient with a period of time.

18. The multifunction device of claim 1, wherein the transmission module is further configured to:
    process a batch sheet associated with the pharmacy, wherein the batch sheet comprises machine-readable information comprising identification information for the pharmacy; and
    retrieve the one or more transmittal instructions that are associated with the pharmacy from the database using the identification information.

19. A multifunction device for generating a prescription, the multifunction device comprising:
    a processor; and
    a processor-readable non-transitory storage medium in communication with the processor, wherein the processor-readable storage medium comprises one or more programming instructions that, when executed, cause the processor to:
    capture information from a plurality of individual cards, wherein one or more of the cards comprises:
        prescription information comprising at least a medication and a dosage for a patient, and
        patient information;
    identifying a key from the captured information,
    using the key to retrieve additional prescription information from a database,
    generating a bitmap file associated with the captured information;
    extracting at least a portion of the prescription information from the bitmap file using optical character recognition;
    extracting physician information from a computer-readable memory,
    assembling the prescription information, the additional prescription information, the patient identification information and the physician information to generate a prescription data file;
    processing a batch sheet associated with a pharmacy, wherein the batch sheet comprises machine-readable information comprising identification information for the pharmacy and one or more transmittal instructions associated with the pharmacy; and
    transmitting the prescription data file to the pharmacy in accordance with the transmittal instructions.

* * * * *